(12) United States Patent  
Tsubata

(10) Patent No.: US 6,447,456 B1  
(45) Date of Patent: Sep. 10, 2002

(54) DEVICE FOR DETECTING PULSE WAVES

(75) Inventor: Keisuke Tsubata, Chiba (JP)

(73) Assignee: Seiko Instruments Inc. (JP)

( * ) Notice: Subject to any disclaimer, the term of this patent is extended or adjusted under 35 U.S.C. 154(b) by 0 days.

(21) Appl. No.: 09/717,858

(22) Filed: Nov. 21, 2000

(30) Foreign Application Priority Data

Dec. 16, 1999 (JP) .......................................... 11-358112

(51) Int. Cl.$^7$ ................................................ A61B 8/00
(52) U.S. Cl. ..................................... 600/455; 600/503
(58) Field of Search ................................ 600/445, 444, 600/441, 446, 449, 454, 501, 502, 503, 455, 456

(56) References Cited

U.S. PATENT DOCUMENTS 5,241,964 A * 9/1993 McQuilkin .................. 600/485
5,669,388 A * 9/1997 Vilkomerson ............... 600/455

* cited by examiner

Primary Examiner—Francis J. Jaworski
Assistant Examiner—Maulin Patel
(74) Attorney, Agent, or Firm—Adams & Wilks

(57) ABSTRACT

A pulse wave detection device capable of accurately detecting pulse waves without influence of noise caused by hand movement or the like has a main sensor disposed on a radial artery and having an emitter for emitting an ultrasonic signal toward the radial artery and a receiver for receiving a reflected ultrasonic signal, and an auxiliary sensor disposed on an ulnar artery and having an emitter for emitting an ultrasonic signal toward the ulnar artery and a receiver for receiving a reflected ultrasonic artery. If the amplitude of an ultrasonic signal received by the main sensor is not between two threshold values, it is determined that detection of pulse waves from the radial artery is difficult. Then detection of pulse waves from the ulnar artery is performed by using the auxiliary sensor. After the lapse of a predetermined period of time from the start of detection using the ulnar artery, the main sensor is again selected to be used. If detection with the main sensor is possible, detection with the main sensor is continued. If detection with the main sensor is difficult even after the predetermined time period, the auxiliary sensor is again selected. If detection with the auxiliary sensor is also difficult, a buzzer is caused to sound to inform the user of this condition.

26 Claims, 10 Drawing Sheets

DEVICE FOR DETECTING PULSE WAVES

BACKGROUND OF THE INVENTION

1. Field of the Invention

The present invention relates to a device for detecting pulse waves and, more particularly, to a pulse wave detection device which detects pulse waves by transmitting ultrasound to an artery and by receiving reflected ultrasound from the artery.

2. Description of the Related Art

Detection of pulse waves of blood flowing in arteries is being widely performed in medical and health care environments. For such pulse wave detection, the method of automatically and electronically determining the pulse rate by using a pulse wave detection device is being widely practiced, as is the method of detecting pulse waves by palpation for a predetermined time period to determine the pulse rate.

Known devices capable of determining the pulse rate by electronically detecting pulse waves are, for example, a device having a piezoelectric element used as a sensor to determine the pulse rate in such a manner that the piezoelectric element is positioned on an artery to detect changes in the pressure of the outermost skin layer (displacements of the skin layer due to the pressure) resulting from changes in the pressure in the artery, and a device utilizing ultrasound to determine the pulse rate.

Pulse wave detection devices utilizing ultrasound include those utilizing the Doppler effect of a flow of blood, e.g., one disclosed in Japanese Patent Application Laid-Open No. Hei 1-214335 and one disclosed in U.S. Pat. No. 4,086,916.

FIGS. 9(a) and 9(b) are diagrams showing changes in the frequency of ultrasound according to the Doppler effect. When ultrasound, such as shown in FIG. 9(a), having a frequency f0, is emitted from a body surface to an artery, the emitted ultrasound is reflected by blood flowing in the artery. The reflected sound is received by a receiving element to detect changes in the frequency of the reflected sound. That is, during a heart contraction period, the speed at which blood flows in the artery becomes high and the frequency of the received sound, indicated by f1, becomes higher (in region A) by the Doppler effect, as shown in FIG. 9(b). Conversely, during a heart relaxation period, the blood flowing speed is low and the frequency of the received sound is low (in region B) relative to that in the region A.

As described above, a bloodstream in an artery, the speed of which changes according to pulsation of the heart, is irradiated with ultrasound, and pulse waves are detected by detecting changes in the frequency of reflected ultrasound, thus enabling determination of the pulse rate, the speed at which blood flows, etc.

To detect pulse waves from an artery at a wrist by the above-described conventional method, a sensor is ordinarily positioned on the radial artery because the existence of the radial artery is generally easily recognizable; the position of the radial artery can be easily determined; and the level of a pulse wave signal detected therefrom is comparatively high.

However, the radial artery on which the sensor is placed is located close to a wrist cord. Therefore, there is a possibility of the sensor being lifted or shifted from the suitable position by a movement of the hand to cause noise, which considerably affects the detection of pulse waves. For this reason, a pulse wave detection error or failure can occur comparatively and easily.

Also, while the facility with which the sensor is positioned is influenced by the shape and the size of the sensor, it is difficult to position the sensor on the some people's wrists. Accordingly, the pulse wave detection performance depends on individual differences of wrists.

SUMMARY OF THE INVENTION

In view of the above-described problems of the conventional art, an object of the present invention is to provide a pulse wave detection device capable of accurately detecting pulse waves without being influenced by noise caused by a movement of the hand or the like.

Another object of the present invention is to provide a pulse wave detection device capable of performing pulse wave detection with reliability regardless individual differences in wrists.

To achieve the above-described objects, according to one aspect of the present invention, there is provided a device for detecting pulse waves, comprising a first sensor having first emitting means for emitting ultrasound toward the radial artery and first receiving means for receiving ultrasound emitted from the first emitting means and reflected by blood flowing in the radial artery, a second sensor having second emitting means for emitting ultrasound toward the ulnar artery and second receiving means for receiving ultrasound emitted from the second emitting means and reflected by blood flowing in the ulnar artery, pulse wave information acquisition means for acquiring pulse wave information on pulse waves from the ultrasound received by one of the first receiving means and the second receiving means, and output means for outputting the pulse wave information acquired by the pulse wave information acquisition means.

Thus, two sensors: the first sensor and the second sensor are provided. Therefore, even if the operation of one of the first and second sensors results in a detection error or detection failure, detection can be performed by using the other of the first and second sensors. For example, if the first sensor is unable to perform detection, the second sensor can be operated to perform detection, thus reducing occurrence of a detection error or failure.

Storage means for storing obtained pulse wave information may be provided. Pulse wave information stored in the storage means can be output afterwards. If pulse wave information obtained as a result of detection during a predetermined period of time is stored, the information can be output to, for example, an external apparatus for a medical diagnosis or the like to be utilized for a medical diagnosis of a user's daily condition.

In the pulse wave detection device according to the present invention, effectiveness determination means may be provided to determine whether the ultrasound received by one of the first receiving means and the second receiving means is effective in detecting pulse wave information. The pulse wave information acquisition means acquires pulse wave information on pulse waves from the ultrasound recognized as effective by the effectiveness determination means. The effectiveness determination means determines the effectiveness of the pulse wave information signals to enable control for selectively acquiring pulse wave information from one of the first and second sensors, thereby reducing occurrence of a detection error or failure.

In the pulse wave detection device according to the present invention, switching means for selectively driving the first sensor or the second sensor may be provided. The switching means selects driving of one of the first and second sensors if it is determined that the ultrasound received by one of the first receiving means and the second receiving means during driving is ineffective. Also, in the pulse wave detection device according to the present invention, the switching means may select driving of the first sensor after a lapse of a predetermined period of time from the time when the switching means selected driving of the second sensor. If this selective drive enabled by the switching means is performed, there is no need to emit ultrasound so that both the first and second sensors always receive ultrasound. Ultrasound may be emitted to be received by only one of the two sensors selectively used, and the consumption of electricity can be reduced.

In the pulse wave detection device according to the present invention, indication means may also be provided. If the effectiveness determination means determines that both the ultrasounds received by the first receiving means and the second receiving means are ineffective, the indication means indicates this condition. This indication means enables the user using the pulse wave detection device to know whether pulse waves are being accurately detected. If the pulse wave detection device is unable to detect pulse waves due to, for example, a failure to maintain the device in the correct position, the user may press a reset button or turn off the power and then turn on the power again, thereby accurately redoing pulse wave detection.

The pulse wave detection device according to the present invention comprises a first sensor having a first transmitter to transmit ultrasound toward the radial artery, and a first receiver to receive ultrasound transmitted from said first transmitter and reflected by blood flowing in the radial artery, a second sensor having a second transmitter to transmit ultrasound toward the ulnar artery, and a second receiver to receive ultrasound transmitted from said second transmitter and reflected by blood flowing in the ulnar artery, a pulse wave information acquisition circuit to acquire pulse wave information on pulse waves from the ultrasound received by one of said first receiver and said second receiver, and an output circuit to output the pulse wave information acquired by said pulse wave information acquisition circuit.

DETAILED DESCRIPTION OF THE PREFERRED EMBODIMENTS

Figure 1A:
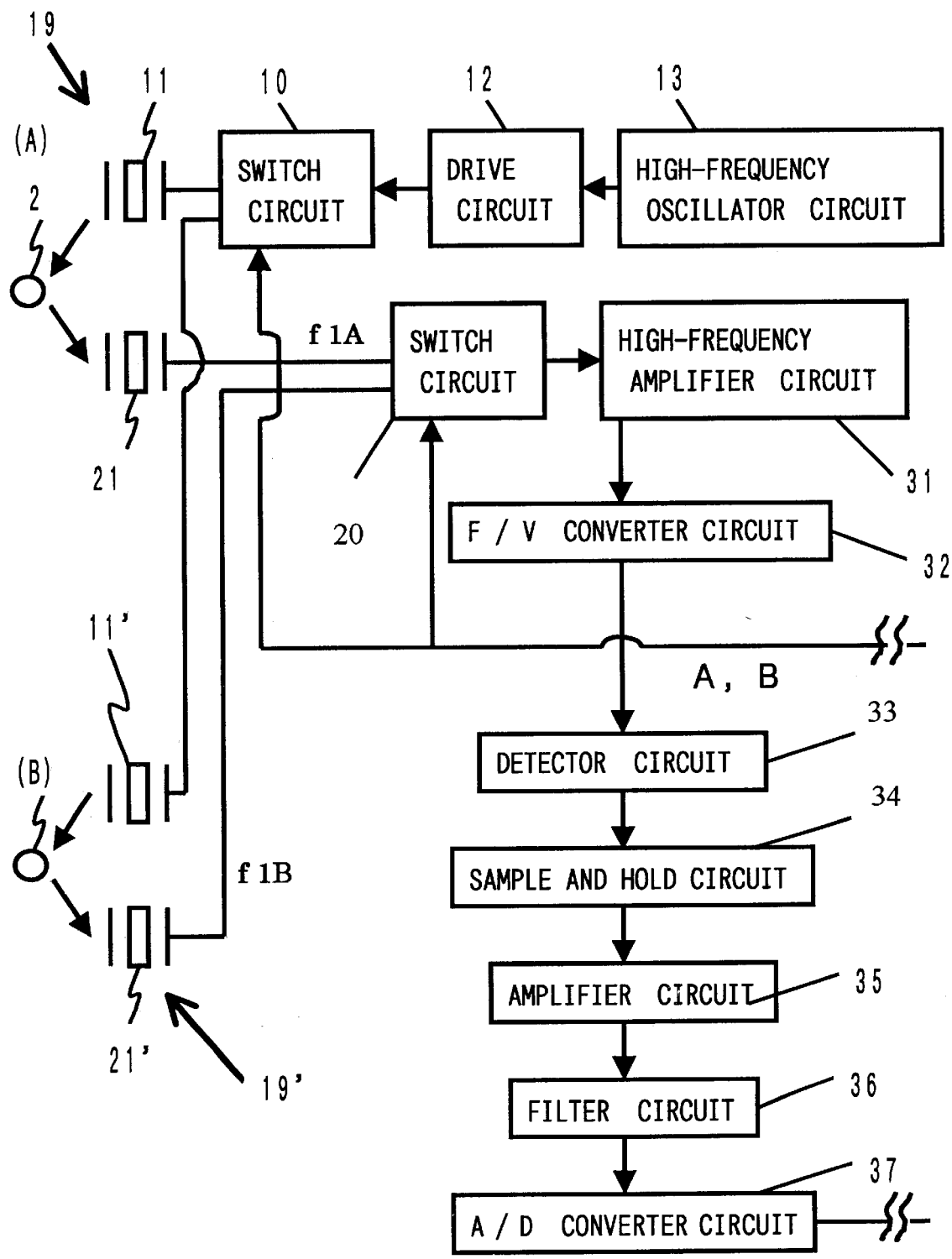
FIGS. 1(a)–1(b) are a diagram showing the configuration of a pulse wave detection device which represents a first embodiment of the present invention.

Preferred embodiments of the present invention will be described in detail with reference to FIGS. 1 through 8.

(1) Outline of Embodiments

A pulse wave detection device according to embodiments of the present invention has two sensors 19 and 19' for emitting ultrasound f0 toward arteries and for, determining pulse rates as pulse wave information from reflected sound f1. The two sensors 19 and 19' are positioned inside a belt of a watch such that they can be positioned on a radial artery 2 and an ulnar artery 3, respectively.

The sensor 19 on the radial artery 2 is used as a main sensor while the sensor 19' on the ulnar artery 3 is used as an auxiliary sensor. Ordinarily, the sensor 19 is used to detect the pulse rate. The sensor 19 has a receiving element 21 which receives reflected sound f1. If the amplitude of reflected wave f1A' obtained as a result of predetermined processing of the received sound signal is not between two threshold values ATh1 and ATh2, it is determined that detection of the pulse rate from the radial artery 2 is too difficult to perform, and the pulse rate is detected from the ulnar artery 3 by using the auxiliary sensor 19'.

The main sensor 19 and the auxiliary sensor 19' are switched by switch circuits 10 and 20 according to selection signals supplied from a control unit 70.

The period of time for detection by the auxiliary sensor 19' is limited to a predetermined fixed time period (e.g., one minute). After a lapse of this time period, the sensor 19 is selected in place of the sensor 19'. If detection with the sensor 19 is possible, detection with the main sensor 19 is continued. If detection with the sensor 19 is difficult even after the lapse of the predetermined time period, the sensor 19' is again switched on in place of the sensor 19. If detection with the sensor 19' is also difficult, a user is informed of this state by a buzzer.

If it is difficult to determine the pulse rate (pulsation information) from the radial artery 2, the pulse rate (pulse information) is determined from the ulnar artery 3. In this manner, occurrence of a pulse wave detection error or failure is reduced and detection is performed with improved accuracy.

(2) Details of Embodiments

Figure 1B:
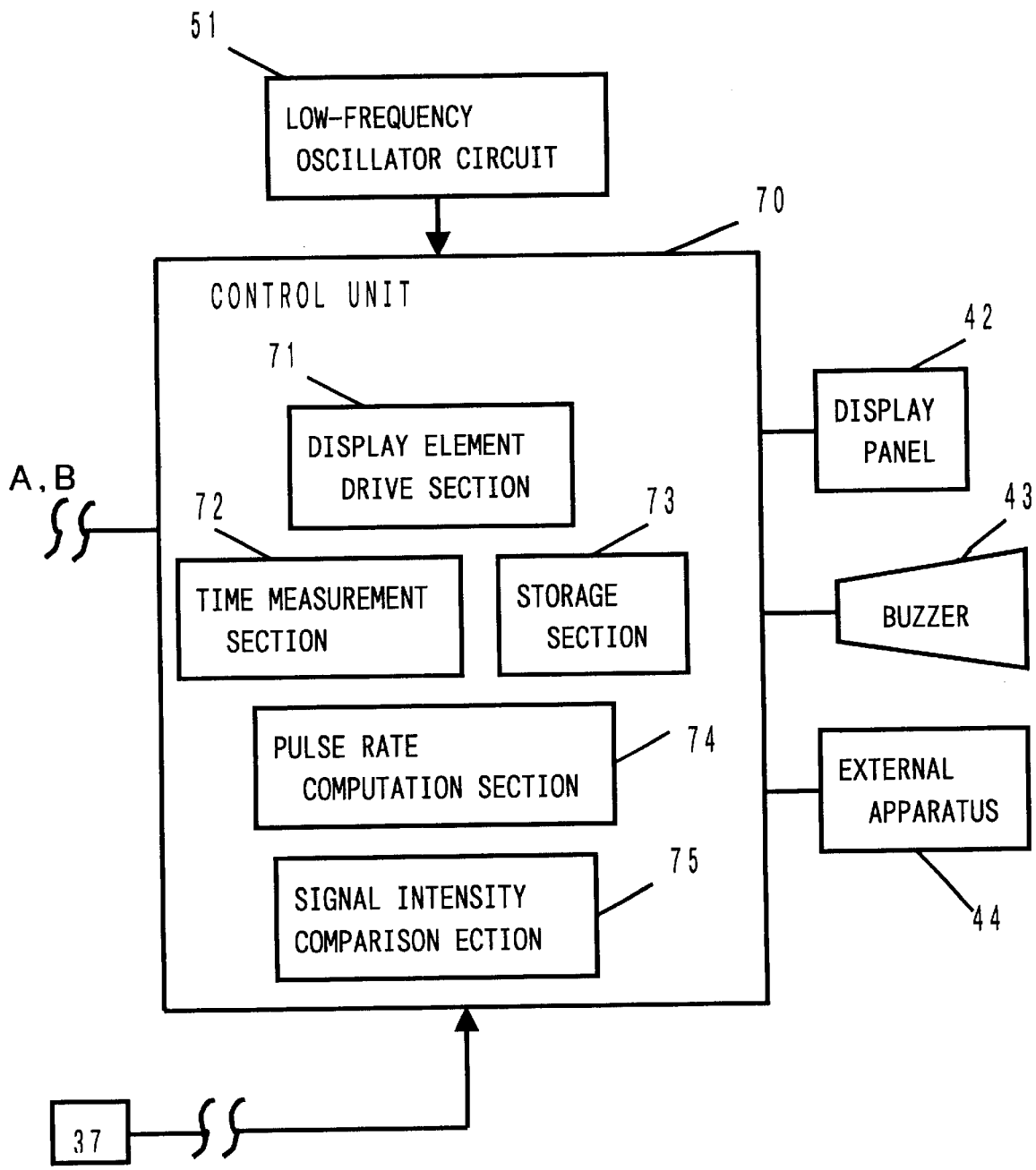

FIGS. 1(a)–1(b) are a diagram showing the configuration of a pulse wave detection device which represents a first embodiment of the present invention.

As shown in FIGS. 1(a)–1(b), the pulse wave detection device has a sensor 19 (first sensor) for detecting pulse waves from the radial artery 2 and a sensor 19, (second sensor) for detecting pulse waves from the ulnar artery 3. The sensor 19 has an emitting element 11 (first emitting means) for emitting ultrasound f0A toward the radial artery 2, and a receiving element 21 (first receiving means) for receiving reflected sound f1A from the radial artery 2. The sensor 19' has an emitting element 11' (second emitting means) for emitting ultrasound f0B toward the ulnar artery 3, and a receiving element 21' (second receiving means) for receiving reflected sound f1B from the ulnar artery 3.

The pulse wave detection device has an emitting system constituted by a switch circuit 10 for selecting one of the emitting elements 11 and 11' to emit ultrasound f0 (generically referred to in place of f0A or f0B, hereinafter) according to a selection signal A or B supplied from a control unit 70, a high-frequency oscillator circuit 13 for generating a high-frequency signal having a frequency of 10 MHz, and a drive circuit 12 for amplifying the high-frequency signal supplied from the high-frequency oscillator circuit 13 so that the signal has a power at an output level, and for emitting ultrasound f0 from the emitting element 11 or 11' selected by the switch circuit 10.

The pulse wave detection device also has a receiving system constituted by a switch circuit 20 for selecting one of the receiving elements 21 and 21' to receive reflected sound f1 according to the selection signal A or B, a high-frequency amplifier circuit 31, a frequency to voltage (F/V) converter circuit 32, a detector circuit 33, a sample and hold circuit 34, an amplifier circuit 35, a filter circuit 36, and analog to digital (A/D) converter circuit 37, and a low-frequency oscillator circuit 51 for generating a signal oscillating at a frequency of 32 kHz. The pulse wave detection device also has the control unit 70.

To the control unit 70, a display panel 42 which functions as an output means to display the pulse rate thereon, and a buzzer 43 are connected. A personal computer and an external apparatus 44 of any kind, such as a diagnosis apparatus for a medical treatment, can also be connected to the control unit 70.

Ultrasound f0A emitted from the emitting element 11 is reflected by blood flowing in the radial artery 2. Simultaneously, ultrasound f0A is frequency-modulated by the flow of blood. Reflected sound f1A obtained is received by the receiving element 21, and a signal representing the received reflected sound f1A is supplied to the switch circuit 20. Similarly, ultrasound f0B emitted from the emitting element 11' is reflected and frequency-modulated by blood flowing in the ulnar artery 3. Reflected sound f1B thus obtained is received by the receiving element 21', and a signal representing the received reflected sound f1B is supplied to the switch circuit 20.

The switch circuit 20 supplies one of the two supplied signals for reflected sounds f1A and f1B to the high-frequency amplifier circuit 31 according to selection control SA or SB.

The high-frequency amplifier circuit 31 is a circuit for amplifying the supplied signal for reflected sound f1 (generically referred to in place of f1A or f1B, hereinafter) and for supplying the amplified signal to the F/V converter circuit 32.

The F/V converter circuit 32 outputs a voltage in accordance with the frequency value by utilizing the change in the voltage gain according to the frequency value, and supplies the voltage to the detector circuit 33.

The detector circuit 34 outputs a voltage corresponding to the envelope of the supplied signal by amplitude detection, and supplies the voltage to the sample and hold circuit 34.

The sample and hold circuit 34 is a circuit for sampling the signal from the detector circuit 33 and for holding sampled signal values.

The filter circuit 36 is a circuit for removing noise from the signal after amplification.

The A/D conversion circuit 37 is a circuit for converting the noise-removed signal into a digital signal, and for supplying the digital signal to the control unit 70 as a processed reflected wave f1' (fundamental signal) used as a basis for detection of pulse wave information.

The control unit 70 is constituted of a microcomputer system whose main components are a central processing unit (CPU), a read only memory (ROM), and a random access memory (RAM), and also has a display element drive section 71, a time measurement section 72, a storage section 73, a pulse rate computation section 74, and a signal intensity comparison section 75.

The signal intensity comparison section 75 functions as an effectiveness determination means, and has threshold values Th1 and Th2 on the amplitude (generically referred to in place of threshold values ATh1 and ATh2 for comparison with the processed reflected wave f1A' and threshold values BTh1 and BTh2 for comparison with the processed reflected wave f1B').

The signal intensity comparison section 75 compares the amplitude of processed reflected wave f1' with the two threshold values Th1 and Th2 to determine the effectiveness of the processed reflected wave f1' supplied from the A/D conversion circuit 37. That is, if the amplitude of the processed reflected wave f1' is not between the threshold values Th1 and Th2, the signal intensity comparison section 75 determines that detection of pulse wave information (pulse rate) from the supplied processed reflected wave f1A' or f1B' is difficult (the signal is ineffective).

In the case where the signal intensity comparison section 75 determines that the processed reflected wave f1A' is ineffective, the control unit 70 supplies the selection signal B to the switch circuits 10 and 20. Conversely, in the case where the signal intensity comparison section 75 determines that the processed reflected wave f1B' is ineffective, the control unit 70 supplies the selection signal A to the switch circuits 10 and 20.

The signal intensity comparison section 75 supplies the display element drive section 71 with a power signal according to the amplitude of the processed reflected wave f1' supplied from the A/D converter circuit 37.

The pulse rate computation section 74 functions as a pulse wave information acquisition means to determine, by a method described below, the pulse rate as pulse wave information from the processed reflected wave f1' having adequate effectiveness determined by the signal intensity comparison section 75.

The display element drive section 71 controls the contents of a display on the display panel 42. It controls a time display made by the time measurement section 72, and displays the pulse rate obtained as pulse wave information in this embodiment. The display element drive section 71 makes a pulse wave power display on the display panel 42 according to the selection signal A or B supplied from the control unit 70 to the switch circuits 10 and 20 and the power signal supplied from the signal intensity comparison section 75.

The time measurement section 72 controls the clock functions of the pulse wave detection device, i.e., a time display function, a time measurement function, etc.

The storage section 73 may use any of various recording mediums, such as a dynamic random access memory (DRAM), a static random access memory (SRAM), an electrically erasable programmable ROM (EEPROM), and a hard disk, for storing data magnetically, electrically or optically. The storage section 73 may have any capacity according to one's need. However, it should have a capacity for storing pulse wave information at least for one hour to twenty-four hours, preferably for one week, more preferably for one month. If pulse wave information obtained over such a predetermined period can be stored in the storage section 73, the pulse wave information stored in the storage section 73 can be outputted and used for a medical diagnosis some days later by being read to the external apparatus 44 connected to the pulse wave detection device.

The storage section 73 may store, for example, pulse wave information obtained from the reflected sounds f1 respectively received by the receiving elements 21 and 21' to enable a diagnosis apparatus for a medical treatment (external apparatus) to obtain pulse wave information over a long period of time and to thereby enable a more accurate diagnosis of the user's condition in daily life from a medial viewpoint.

Information on times at which pulse wave information is stored is supplied from the time measurement section 72 and stored in the storage section 73 together with the pulse wave information, thereby enabling a diagnostician to know the condition of pulsation at each time.

The operation of the above-described embodiment will now be described.

The principle of detection of pulse waves from ultrasound emitted to the radial artery 2 and the ulnar artery 3 and frequency-modulated by the Doppler effect according to the speed at which blood flows will first be described.

The speed at which blood flows in the artery changes with alternation of the heart contraction period (pulse) and the heart relaxation period. Therefore, the frequency of ultrasound emitted to the flow of blood is changed by the Doppler effect when the ultrasound is reflected by the flow of blood.

If the frequency of the ultrasound is f0; the speed at which blood flows is v; the sound velocity in the body is c; and the angle of incidence of the ultrasound on the blood flowing speed is θ, then the frequency f1 of the reflected sound is obtained by the following equation 1:

$$f1 = f0(1 + 2v \times \cos \theta/c) \quad (1)$$

The frequency of the ultrasound ranges from f0 to f1 by reflection, and the deviation df of the frequency is expressed by the following equation 2:

$$df = f1 - f0 = f0 \times 2v \times \cos \theta/c \quad (2)$$

As a result, if, for example, c=155 m/s; v=0.3 m/s; and f0=9.5, the frequency deviation df is 3.8 KHz.

According to the equation 2, since the blood flowing speed v is changed by pulsation, the frequency deviation df changes through the range of about 2 to 4 kHz.

In this embodiment, changes in this frequency deviation df are detected by a frequency-modulated sound demodulation system, thereby detecting pulse waves.

FIGS. 2(a) through 2(d) are diagrams showing waveforms output from the essential components of the pulse wave detection device.

Figure 2A:
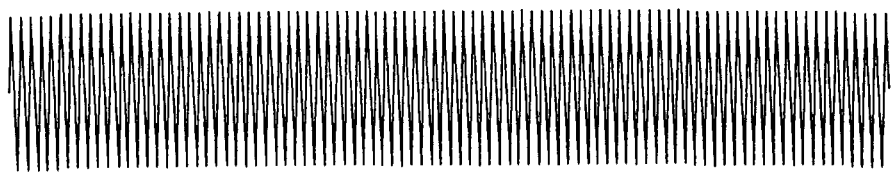
FIGS. 2(a) through 2(d) are diagrams showing waveforms output from the essential components of the pulse wave detection device shown in FIG. 1.

The high-frequency oscillator circuit 13 generates, from its internal portion, ultrasound f0 which is a high-frequency signal having a frequency of 10 MHz, as shown in FIG. 2(a).

Figure 2B:

Ultrasound f0 is emitted to blood flowing in the artery, and sound f1 reflected by the blood is frequency-modulated by the Doppler effect when it is reflected. Reflected and frequency-modulated sound f1 is received by the receiving element 21 or 21', as shown in FIG. 2(b).

Figure 2C:
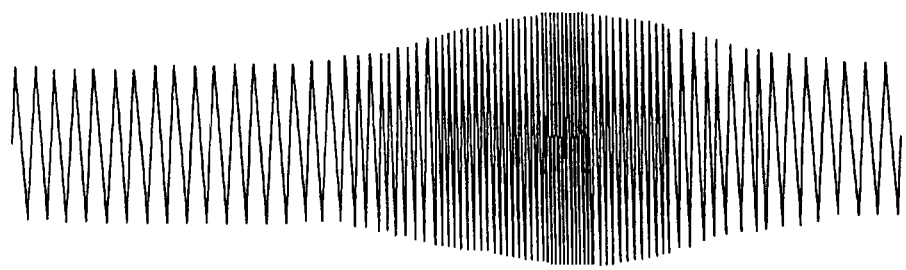

A signal representing this reflected sound f1 is amplified by the high-frequency amplifier 31 and is thereafter supplied to the F/V converter circuit 32. The F/V converter circuit 32 converts a change in the frequency of the reflected sound f1 signal into a change in voltage, i.e., a change in the amplitude as shown in FIG. 2(c), and supplies the converted signal to the detector circuit 33.

Figure 2D:

The detector circuit 33 obtains a continuous signal such as shown in FIG. 2(d) from the signal supplied from the F/V converter circuit 32, and supplies the obtained signal to the amplifier circuit 35. The signal output from the detector circuit 33 is amplified by the amplifier circuit 35, is processed by the filter circuit 36 to remove noise components, and is converted into a digital signal by the A/D converter circuit 37. This digital signal is supplied as processed reflected wave f1' to the control unit 70.

The control unit 70 determines the effectiveness of the processed reflected wave f1' supplied to it, and determines, by processing in the pulse rate computation section 74, the pulse rate as pulse wave information from the processed reflected wave f1A' or f1B' having adequate effectiveness.

The principle of determination of the pulse rate from the reflected wave f1' obtained by processing the received ultrasound will now be described.

In the pulse rate computation section 74, a pulse is generated by, for example, a comparison circuit when the level of the processed reflected wave f1' becomes higher than a reference value, and time intervals at which pulses are generated in this manner are measured a predetermined number of times (e.g., three times, five times, seven times, or ten times). An average time T is obtained by averaging the time periods measured in this manner. The number N of pulse waves during one minute is obtained by the following equation 3:

$$N = 60/T \quad (3)$$

This method of obtaining the pulse rate from the average time T of the time intervals of pulse waves is not exclusively used. For example, a method may alternatively be used in which the number w of pulses generated during a predetermined time period t (e.g., ten seconds) is detected and the number N of pulse waves during one minute is obtained by the following equation 4:

$$N = w \times (60/t) \quad (4)$$

The pulse rate computation section 74 supplies the display element drive section 71 with the obtained number N of pulse waves and pulse signals generated in correspondence with the pulse waves.

Figure 3A:
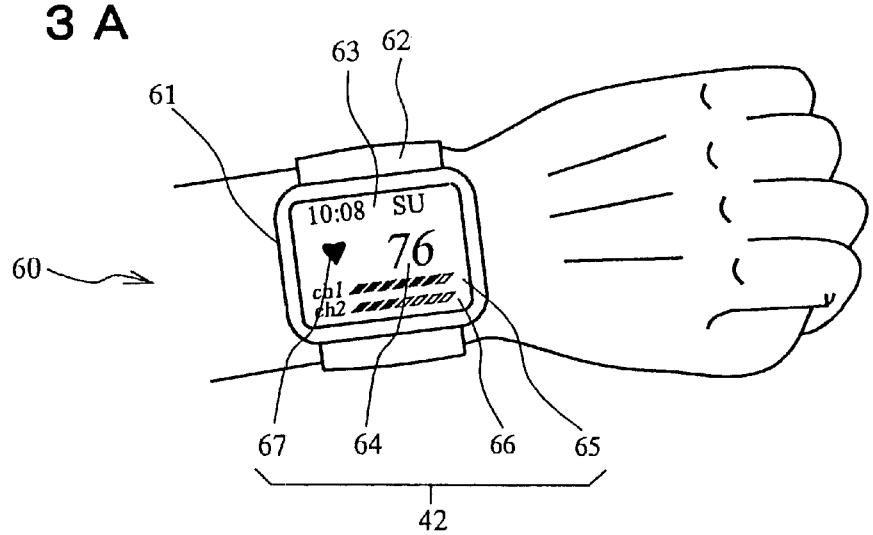
FIGS. 3(a) through 3(c) are diagrams showing a state where pulse waves are detected by a pulse wave detection device incorporated in a watch according to the first embodiment.
Figure 3B:
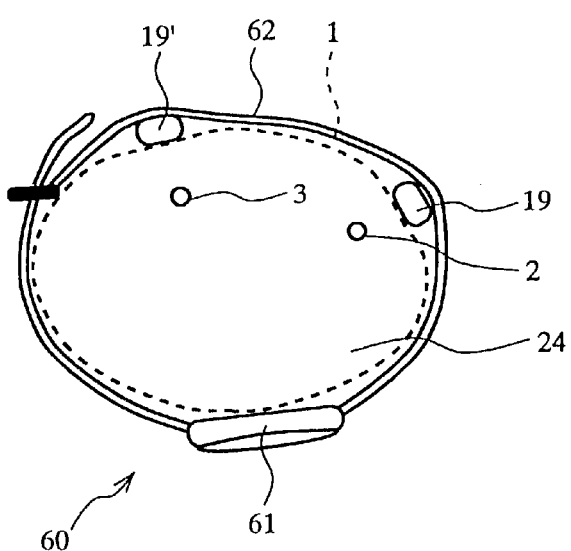
Figure 3C:
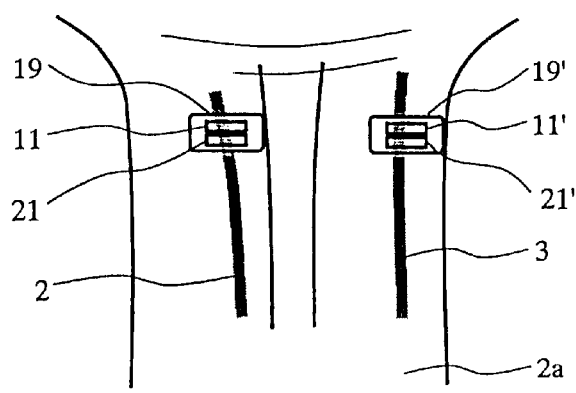
Figures 4A, 4B:
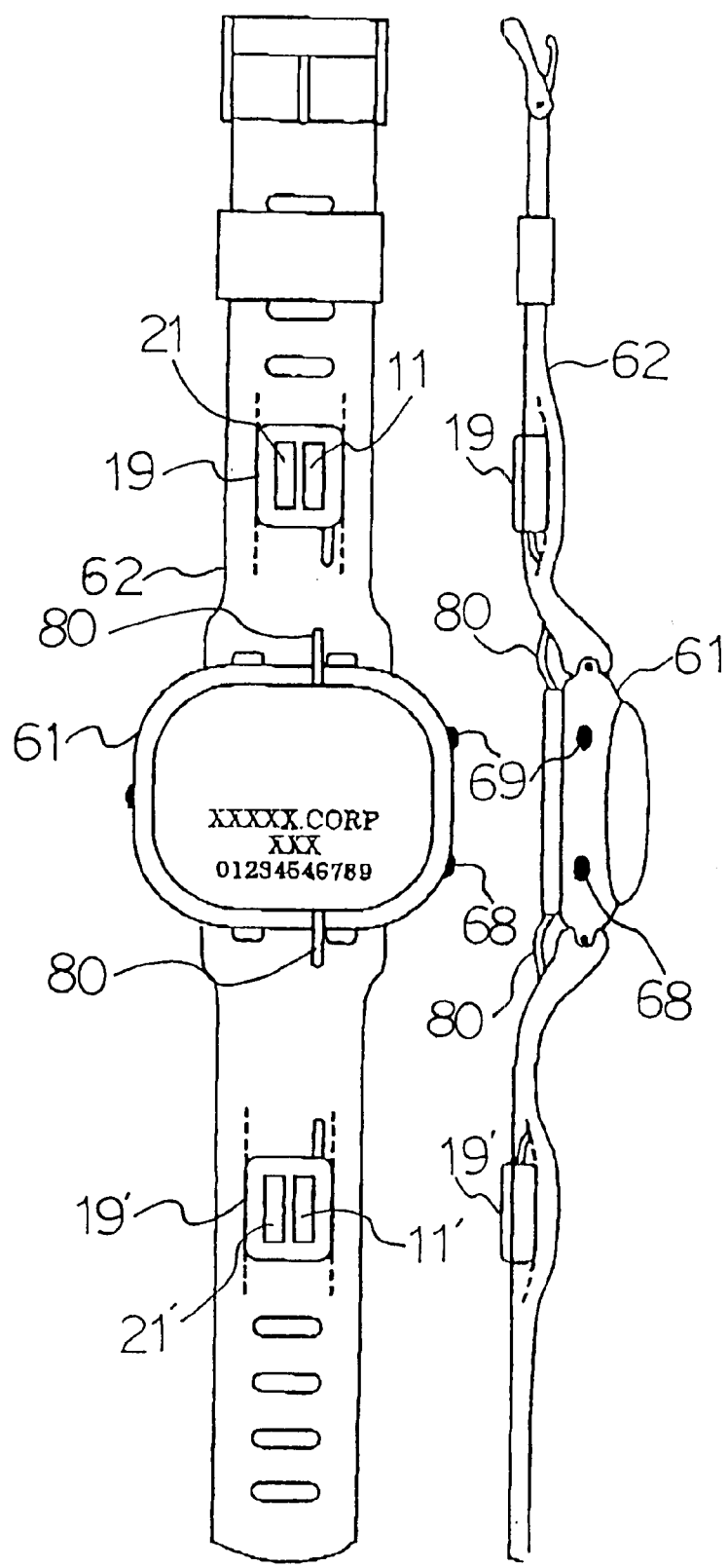
FIGS. 4(a) and 4(b) are diagrams showing an external appearance of the pulse wave detection device (watch) shown in FIGS. 3(a) through 3(c)

FIGS. 3(a), 3(b), and 3(c) are diagrams showing a state where pulse waves are detected by a pulse wave detection device incorporated in a watch 60 according to this embodiment. FIGS. 4(a) and 4(b) are diagrams showing an external appearance of the pulse wave detection device (watch) 60.

As shown in FIGS. 3(a) to 3(c) and FIGS. 4(a) and 4(b), the pulse wave detection device (watch) 60 has a watch body 61 and a belt 62, and sensors 19 and 19' are attached to inner portions of the belt 62.

As shown in FIG. 3(a), the watch 60 is fitted around a left (or right) wrist 2a like an ordinary watch, with the watch body 61 placed on the side corresponding to the back of the hand. The sensors 19 and 19' can be positioned by being moved in the longitudinal direction of the belt 62 so that the sensor 19 is positioned on the radial artery 2 while the sensor 19' is positioned on the ulnar artery 3 when the watch is worn, as shown in FIG. 3(b).

As shown in FIG. 3(c) and FIG. 4(a), the emitting element 11 and the receiving element 21 of the sensor 19 are disposed side by side along the radial artery 2 and in a direction perpendicular to the longitudinal direction of the belt 62, and the emitting element 11' and the receiving element 21' of the sensor 19' are disposed in the same manner along the ulnar artery 3. The emitting elements 11 and 11' are located on the forearm distal sides of the sensors while the receiving elements 21 and 21' are located on the forearm proximal side. The order of the emitting elements 11 and 11' and the receiving elements 21 and 21' in the direction along the arteries may be reversed.

As shown in FIGS. 3(c) and 4(a), the face of each of the emitting elements 11 and 11' and the receiving elements 21 and 21' to be brought into contact with the wrist body surface is formed into a rectangular shape and is positioned along the longitudinal direction of the belt 62 so that its longitudinal axis perpendicularly intersects the radial artery 2 or ulnar artery 3.

Drive components, i.e., a watch movement, etc., are provided in the watch body 61. In the watch body 61 are also provided a drive circuit 12, a high-frequency oscillator circuit 13, switch circuits 10 and 20, a high-frequency amplifier circuit 31, an F/V converter circuit 32, a detector circuit 33, a sample and hold circuit 34, an amplifier circuit 35, a filter circuit 36, an A/D converter circuit 37, a control unit 70, a display panel 42, and a low-frequency oscillator circuit 51. A reset button 68 and a switching button 69 are provided in side portions of the watch body 61 (see FIGS. 4(a) and 4(b)). The low-frequency oscillator circuit 51 has the same oscillation frequency as a drive circuit used for clock functions. Therefore, a common oscillator circuit may be formed for both the pulse wave detection function and the clock functions.

The sensors 19 and 19' provided on the belt 62 and the switch circuits 10 and 20 provided in the watch body 61 are connected by wiring 80 laid in the belt 62 as shown in FIGS. 4(a) and 4(b).

In a display surface (face) of the watch body 61, a watch display 63 on which time and other information (a day, a day of the week, etc.) are displayed, and the display panel 42 are provided. The display panel 42 has a pulse rate display portion 64 on which the number N of pulse waves is displayed, a pulsation on-and-off signaling portion 67 with a lighting means which is turned on and off according to pulsation, and pulsation display portions 65 and 66 for displaying the intensity of the pulsation signal.

On the pulsation display portion 65 (ch1), the intensity of the pulsation signal obtained as a result of pulse wave detection from the radial artery 2 is displayed. On the pulsation display portion 66 (ch2), the intensity of the pulsation signal obtained as a result of pulse wave detection from the ulnar artery 3 is displayed. The pulsation display portions 65 and 66 are alternatively activated for display. When selection signal A is supplied from the control unit 70 to the switch circuits 10 and 20, the pulsation display portion 65 is activated for display. When selection signal B is supplied, the pulsation display portion 66 is activated for display.

In a scale of 0 to 100 from the left end to the right end on each of the pulsation display portions 65 and 66, the signal intensity is indicated at a larger scale value if the signal intensity is higher. The indicated scale value is determined by the display element drive section 71 according to the power signal supplied from the signal intensity comparison section 75.

A user can know the state of detection of pulsation through the receiving elements 21 and 21' from a display in the scale on the pulsation display portion 65 or 66. The user can also know, from the scale value on the pulsation display portion 65 or 66, whether the number N of pulse waves displayed on the pulse rate display portion 64 is a value obtained by detection from the radial artery 2 or a value obtained by detection from the ulnar artery 3.

The color of on-and-off lighting each of the pulsation display portions 65 and 66 may be changed according to the number of pulse waves. For example, on-and-off lighting in yellow is performed when the number of pulse waves is 69 or smaller; on-and-off lighting in blue when the number of pulse waves is 70 to 90; on-and-off lighting in green when the number of pulse waves is 91 to 110; on-and-off lighting in orange when the number of pulse waves is 111 to 130; and on-and-off lighting in red when the number of pulse waves is 131 or greater. The condition of pulsation can be easily recognized discriminatingly from such display colors set with respect to the number of pulse waves.

The switching button 69 attached to the watch body 61 is used to change displays made on the watch display 63 and the display panel 42 for displaying the number N in such a manner that, for example, time and pulse rate information are simultaneously displayed in the display surface of the watch 60 or displayed separately from each other. The reset button 68 attached to the watch body 61 is pressed to reset the detection device in a case where the detection device is unable to perform pulse wave detection from the radial artery 2 or ulnar artery 3, thereby retrying accurate detection of pulse waves from the radial artery 2 or ulnar artery 3.

Figure 5:
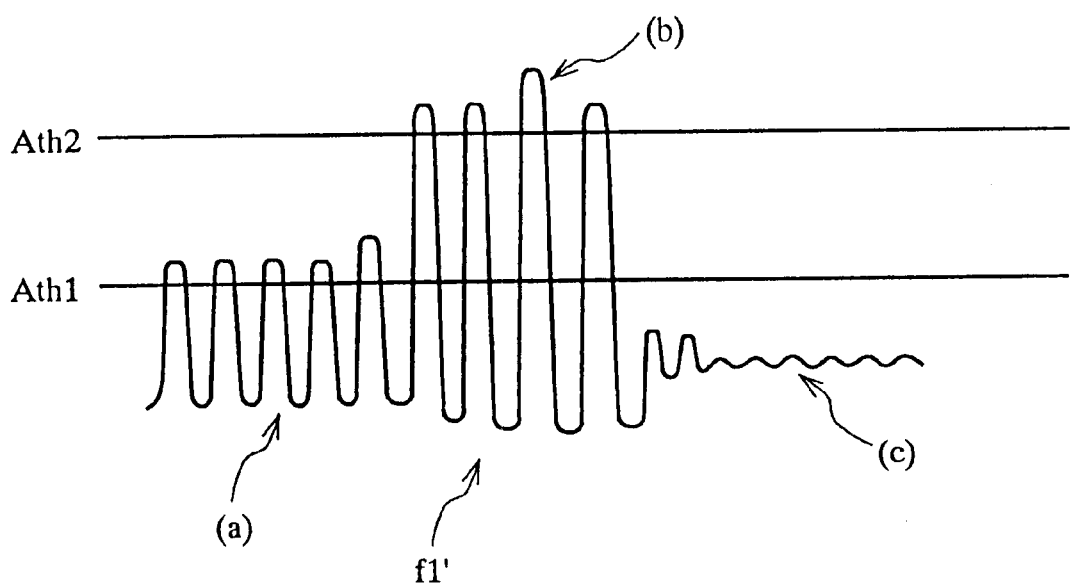
FIG. 5 is a diagram for explaining the principle of changing arteries from which pulse waves are detected.

FIG. 5 is a diagram for explaining the principle of determination in the signal intensity comparison section 75 as to whether the processed reflected wave f1' is effective in detecting pulse waves. Although the processed reflected wave f1' is converted into a digital signal, it is shown as an analog signal in FIG. 5 for ease of understanding.

A case in which pulse wave information (the number of pulses) is detected from the radial artery 2 will be described by way of example with reference to FIG. 5.

In this embodiment, adequate effectiveness is recognized if the amplitude. of the processed reflected wave f1A' supplied from the A/D converter circuit 37 is between the two threshold values ATh1 and ATh2 previously set for measurement on the radial artery 2.

The amplitude of the processed reflected wave f1A' obtained by detection from the radial artery 2 is sometimes so small that it does not reach the first threshold value ATh1 designating the necessary amplitude for detection of pulse. waves, as indicated by (c) in FIG. 5. Such a condition results from a shift of the pulse wave detection device from the correct position, weak pulsation in the radial artery 2, etc. Also, the amplitude of the processed reflected wave f1A' obtained by detection from the radial artery 2 can exceed the second threshold value ATh2, as indicated by (b) in FIG. 5, when influenced by large noise caused by movements of fingers or the like, a shift of the sensor 19 from the correct position, separation from the body surface, etc, resulting in failure to accurately detect pulse waves.

Therefore, adequate, effectiveness of the processed reflected wave f1A' in obtaining accurate pulse wave information from the radial artery 2 is recognized when the amplitude of the signal is between the two threshold values ATh1 and ATh2, as indicated by (a) in FIG. 5. Adequate effectiveness is not recognized in other cases (difficulty of measurement is recognized).

In this embodiment, the sensor 19 is first used as a main sensor to obtain pulse wave information from the radial artery 2. If the result of determination by the signal intensity comparison section 75 is that the processed reflected wave f1A' is ineffective as shown in FIG. 5, the selection signal B is supplied from the control unit 70 to the switch circuits 10 and 20 to select the sub sensor (auxiliary sensor), i.e., the sensor 19' in place of the main sensor 19 and to select the ulnar artery 3 in place of the radial artery 2 as an object from which pulse wave information is to be obtained.

Similarly, in the signal intensity comparison section 75, adequate effectiveness of the processed reflected wave f1B' supplied from the A/D converter circuit 37 is recognized when the amplitude of the signal is between the two threshold values BTh1 and BTh2 with respect to the ulnar artery 3. Adequate effectiveness is not recognized when the amplitude of the signal is not between the two threshold values BTh1 and BTh2 (difficulty of measurement is recognized). In this embodiment, if the result of determination by the signal intensity comparison section 75 is that measurement of pulse waves on the ulnar artery 3 with the sensor 19' is difficult, a warning sound is output by the buzzer 43 under the control of the control unit 70.

Figure 6:
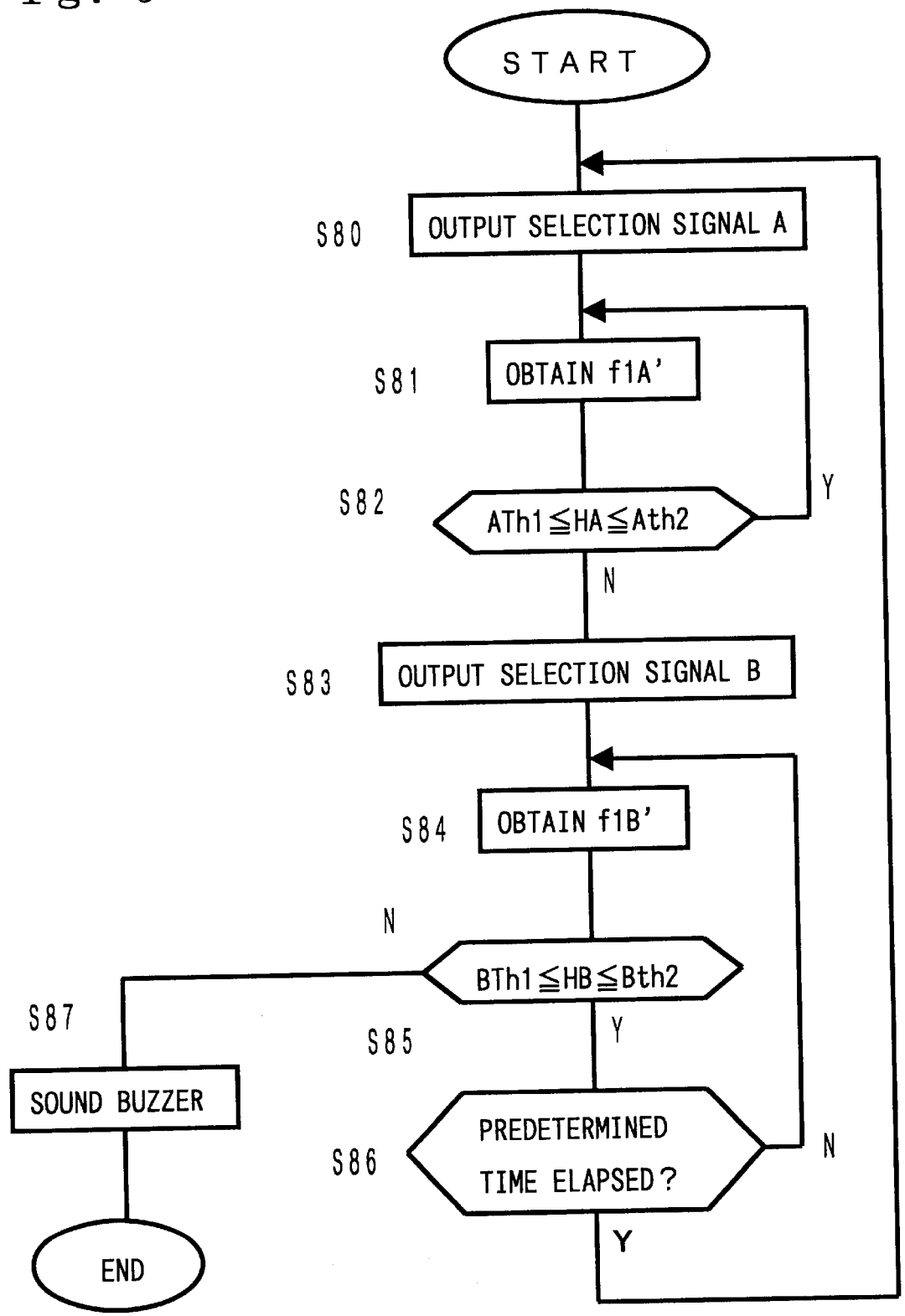
FIG. 6 is a flowchart showing the process performed by a signal intensity comparison section.

FIG. 6 is a flowchart showing the process performed by the control unit 70 to change the measurement object.

First, the control unit 70 of the pulse wave detection device supplies selection signal A to the switch circuits 10 and 20 (step S80), thereby driving the main sensor 19 and obtaining from the A/D conversion circuit 37 the processed reflected wave f1A' obtained by detection from the radial artery 2 (step S81).

The control unit 70 then determines by the signal intensity comparison section 75 the effectiveness of the obtained processed reflected wave f1A'. That is, the signal intensity comparison section 75 makes a determination (step 82) as to whether, if the amplitude of the processed reflected wave f1A' is HA, ATh1≦HA≦ATh2 is satisfied, that is, whether the amplitude HA of the processed reflected wave f1A' is between the two threshold values ATh1 and ATh2 with respect to the radial artery 2, which defines the effectiveness of the signal.

If it is determined that the processed reflected wave f1A' is effective (step S82; Y), the control unit 70 returns to step 81 to continue processing for determining the effectiveness of the processed reflected wave f1A'. Simultaneously, the control unit 70 performs processing for obtaining pulse wave information on the basis of the processed reflected wave f1A' obtained by detection from the radial artery 2 and having adequate effectiveness recognized, i.e., processing for making a display on the display panel 42 (displaying the number N of pulse waves on the pulse rate display portion 64, on-and-off lighting of the pulsation on-and-off signaling portion 67 according to pulsation, and displaying the pulsation signal intensity on the pulsation display portion 65 (ch1)). The control unit 70 also stores the displayed pulse wave information in the storage section 73.

On the other hand, if it is determined that the processed reflected wave f1A' is ineffective (HA<ATh1 or HA>ATh2) by the signal intensity comparison section 75 (step S82; N), the measurement on the radial artery 2 can not be continued. The control unit 70 then outputs selection signal B to the switch circuits 10 and 20 to select the ulnar artery 3 as a measurement object (step S83). The control unit 70 obtains the time at which selection signal B is output from the time measurement section 72 and stores it in a RAM (not shown).

Receiving selection signal B,. the switch circuit 10 connects the emitting element 11, to the drive circuit 12 while disconnecting the emitting element 11 from the drive circuit 12, and the switch circuit 20 connects the receiving element 21' to the high-frequency amplifier circuit 31 while disconnecting the receiving element 21 from the high-frequency amplifier circuit 31.

The control unit 70 changes the drive for driving the sub sensor 19', and obtains from the A/D converter circuit 37 the processed reflected wave f1B' obtained by detection from the ulnar artery 3 (step S84).

The control unit 70 then determines by the signal intensity comparison section 75 the effectiveness of the obtained processed reflected wave f1B'. That is, the signal intensity comparison section 75 makes a determination (step S85) as to whether, if the amplitude of the processed reflected wave f1B' is HB, BTh1≦HB≦BTh2 is satisfied, that is, whether the amplitude HB of the processed reflected wave f1B' is between the two threshold values BTh1 and BTh2 with respect to the ulnar artery 3, which defines the effectiveness of the signal.

If it is determined that the processed reflected wave f1B' is effective (step S85; Y), the control unit 70 compares the present time of the time measurement section 72 with the time stored in the RAM to determine whether the predetermined time period has elapsed after the time when selection signal B was output (step S86). In this embodiment, the predetermined time period for detection of pulse waves from the ulnar artery 3 by using the sub sensor 19' is set to one minute. However, any other time period (e.g., two minutes, three minutes, five minutes, ten minutes, or n minutes set according to one's need) may alternatively be set.

If the predetermined time period has not yet elapsed (step S86; N), the control unit 70 returns to step 84 to continue processing for determining the effectiveness of the processed reflected wave f1B'. Simultaneously, the control unit 70 performs processing for obtaining pulse wave information on the basis of the processed reflected wave f1B' obtained by detection from the ulnar artery 3 and having adequate effectiveness recognized, i.e., processing for making a display on the display panel 42 (displaying the number N of pulse waves on the pulse rate display portion 64, on-and-off lighting of the pulsation on-and-off signaling portion 67 according to pulsation, and displaying the pulsation signal intensity on the pulsation display portion 66 (ch2)). The control unit 70 also stores the displayed pulse wave information in the storage section 73. Since the pulsation display portion 66 has been activated for display of the pulsation signal intensity display in place of the pulsation display portion 65, the user can understand that the measurement object has been changed, that is, the ulnar artery 3 has been selected in place of the radial artery 2.

After the predetermined time period has elapsed (step S86; Y), the control unit 70 returns to step 80 to again select the radial artery 2 as the object of measurement with the main sensor 19 in place of the ulnar artery 3 with the sub sensor 19'.

With the passage of the predetermined time period from the start of measurement on the ulnar artery 3, the conditions of the positional relationship between the radial artery 2 and the sensor 19, etc., necessary for measurement, are ordinarily restored. Therefore, selection signal A is output to the switch circuits 10 and 20 to restart measurement on the radial artery 2.

If the processed reflected wave f1A' is ineffective even after the control unit 70 returned to step S80 and switching has been performed to again start measurement on the radial artery 2 (step S82; N), pulse wave detection from the ulnar artery 3 is continued as long as the measurement on the ulnar artery 3 is effective, and determination is periodically made (at constant time intervals) as to whether measurement on the radial artery 2 is possible.

If it is determined in step 85 that the processed reflected wave f1B' is ineffective (HB<BTh1 or HB>BTh2) (step S85; N), both measurement on the radial artery 2 and measurement on the ulnar artery 3 are difficult to perform. The control unit 70 then outputs buzzer sound from the buzzer 43 (step S87) and terminates the pulse wave detection process.

In the case where the buzzer 43 sounds because both measurement on the radial artery 2 and measurement on the ulnar artery 3 are difficult, the user may press the reset button 68 (See FIGS. 4(a) and 4(b) attached to the watch body 61 to restart detection of pulse waves.

A second embodiment of the present invention will be next be described.

Figure 7:
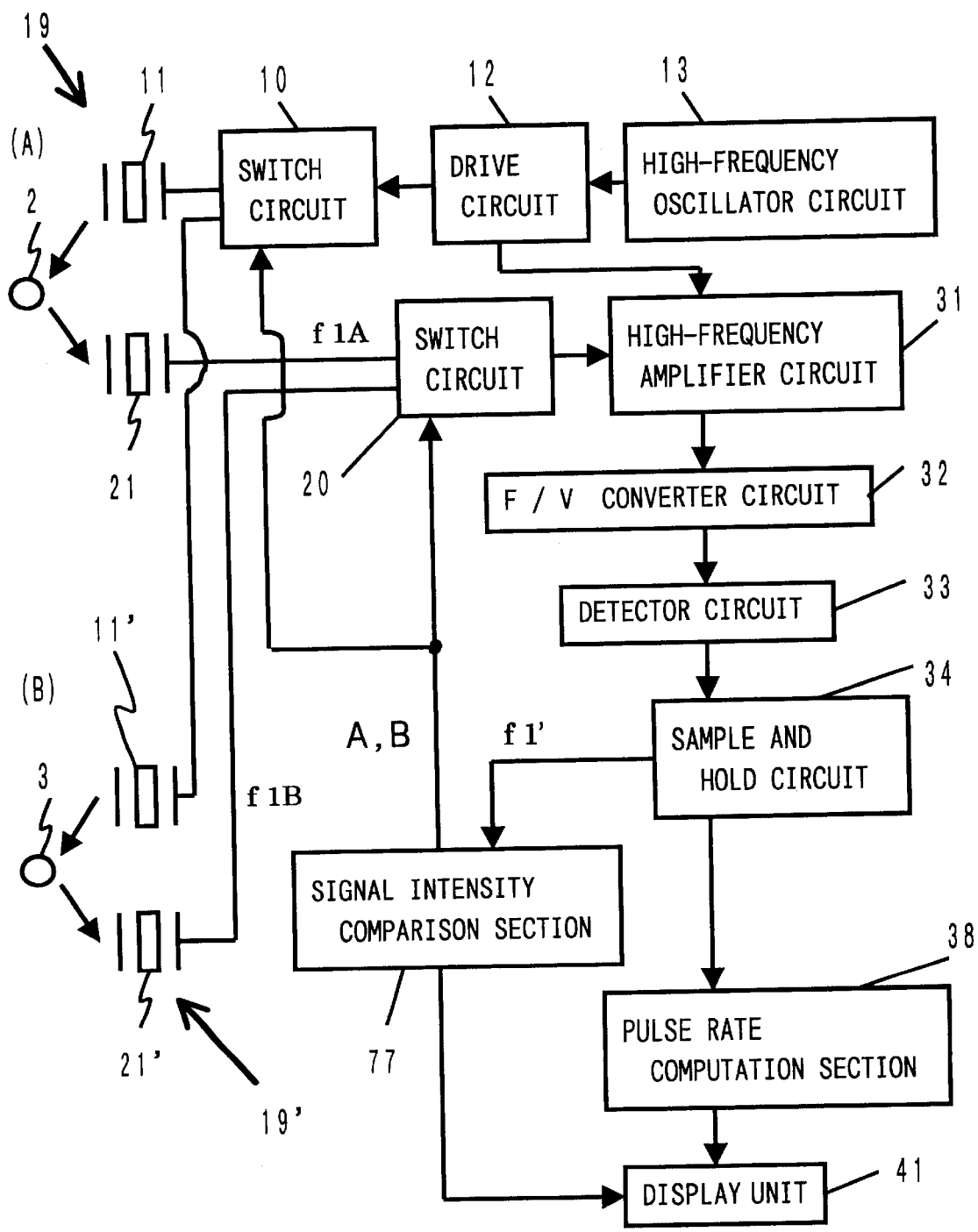
FIG. 7 is a diagram showing the configuration of a pulse wave detection device which represents a second embodiment of the present invention.

FIG. 7 is a diagram showing the configuration of a pulse wave detection device which represents the second embodiment of the present invention. Components of this embodiment identical or corresponding to those of the first embodiment are indicated by the same reference characters, and the description for them will not be repeated.

The second embodiment differs in configuration from the first embodiment but operates in the same manner as the first embodiment.

In this embodiment, as shown in FIG. 7, a pulse rate computation circuit 38, a display unit 41 and a signal intensity comparison circuit 77 are provided.

The signal intensity comparison circuit 77 is a circuit for determining the effectiveness of processed reflected wave f1' supplied from a sample and hold circuit 34. That is, the signal intensity comparison circuit 77 corresponds to the control unit 70 in the first embodiment. If the amplitude of processed reflected wave f1' is not between threshold values Th1 and Th2, the signal intensity comparison circuit 77 determines whether detection of pulse wave information on the basis of processed reflected wave f1A' or f1B' presently supplied is effective.

If the signal intensity comparison circuit 77 determines that processed reflected wave f1A' is ineffective, it supplies selection signal B to switch circuits 10 and 20. If the signal intensity comparison circuit 77 determines that processed reflected wave f1B' is ineffective, it supplies selection signal A to the switch circuits 10 and 20.

The pulse rate computation circuit 38 is a circuit for obtaining the pulse rate as pulse wave information from the processed reflected wave f1' having adequate effectiveness determined by the signal intensity comparison circuit 77. This pulse rate computation circuit 38 corresponds to the pulse rate computation section 74 in the control unit 70 in the first embodiment.

The display unit 41 has the same function as a watch, i.e., the function of displaying time (a day, a day of the week, etc.), and also has a function of displaying the pulse rate as pulse wave information obtained by the pulse rate computation circuit 38.

In the second embodiment, as described above, the signal intensity comparison circuit 77 also switches main sensor 19 and sub sensor 19' to reduce occurrence of a pulse wave detection error or failure and to enable more accurate detection of pulse waves, as does the corresponding component in the first embodiment.

A third embodiment of the present invention will be next be described.

A pulse wave detection device according to the third embodiment has the same configuration as the pulse wave detection device shown in FIG. 1 or 7, but operates in a different way. In the third embodiment, the effectiveness of each of processed reflected waves f1A' and f1B' is determined by equally handling sensor 19 on radial artery 2 and sensor 19' on ulnar artery 3 without setting sensors 19 and 19' as main and sub sensors, and the pulse rate is detected as pulse wave information from one of sensors 19 and 19' having adequate effectiveness or a higher degree of effectiveness.

If the pulse wave detection device is formed as shown in FIG. 1, signal unit 70 first outputs selection signal A and outputs selection signal B after a lapse of a predetermined time period (e.g., two seconds) to obtain each of processed reflected waves f1A' and f1B' for a certain time period (e.g., two seconds).

Signal intensity comparison section 75 successively determines the effectiveness of processed reflected waves f1A' and f1B', and determines, as a measurement object, one of processed reflected waves f1A' and f1B' having a degree of effectiveness adequately high and higher than that of the other.

If processed reflected wave f1A' is determined as a measurement object, control unit 70 again outputs selection signal A. If processed reflected wave f1B' is determined as a measurement object, measurement on the basis of processed sound signal f1B' presently supplied from A/D converter circuit 37 is continued.

If the pulse wave detection device is formed as shown in FIG. 7, control unit 70 first outputs selection signal A and then outputs selection signal B after a lapse of a predetermined time period (e.g., two seconds) to obtain each of processed reflected waves f1A' and f1B' for a certain time period (e.g., two seconds).

Signal intensity comparison circuit 77 successively determines the effectiveness of processed reflected waves f1A' and f1B', and determines, as a measurement object, one of processed reflected waves f1A' and f1B' having a degree of effectiveness adequately high and higher than that of the other.

If processed reflected wave f1A' is determined as a measurement object, control unit 70 again outputs selection signal A. If processed reflected wave f1B' is determined as a measurement object, outputting of selection signal B is not specially performed since selection signal B has already been output and since processed reflected wave f1B' is presently being supplied to pulse rate computation circuit 38.

Then measurement is continuously performed by using the processed reflected wave f1' with which a higher degree of effectiveness has been recognized in the first place (e.g., processed reflected wave f1A'). Thereafter, if it is determined that the processed reflected wave f1' used for the measurement is not effective, selection signal A or B is output to select sensor 19 or 19' by switch circuits 10 and 20, and measurement using the other processed reflected wave f1' is continuously performed as long as the other processed reflected wave f1' is effective.

For example, if measurement is started by first determining that the effectiveness of processed reflected wave f1A' is higher, pulse wave measurement is continued on the basis of processed reflected wave f1A' obtained by detection from radial artery 2 with sensor 19. If it is determined that there is no effectiveness of processed reflected wave f1A' used for the measurement due to a movement of the hand or body, etc., selection signal B is output to switch circuits 10 and 20 to select pulse wave measurement based on processed reflected wave f1B' obtained by detection from ulnar artery 3 with sensor 19'. In the third embodiment, sensors 19 and 19' are not discriminated from each other as main and sub sensors. Therefore, if processed reflected wave f1B' is effective even after a lapse of the predetermined time period (one minute in the first and second embodiments), the same measurement is continued.

A fourth embodiment of the present invention will be described.

Figure 8A:
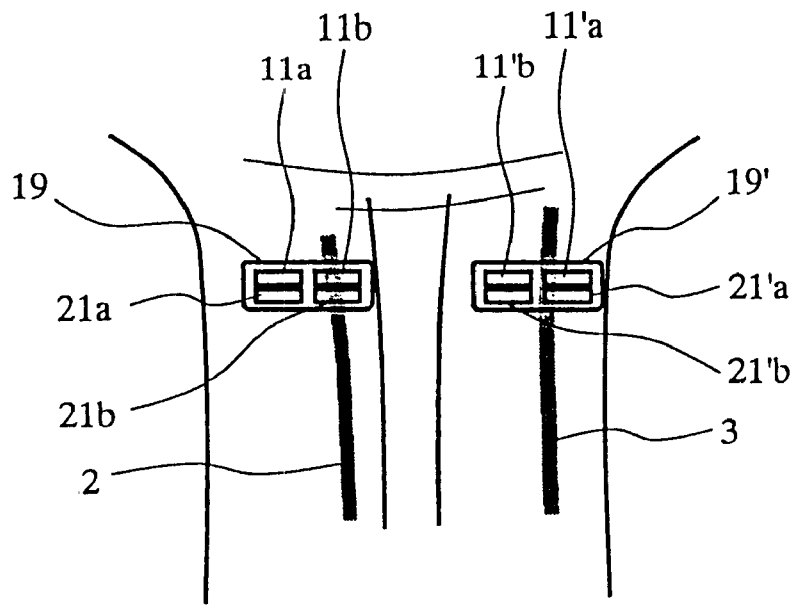
FIGS. 8(a) and 8(b) are diagrams showing examples of modification of sensors.
Figure 8B:
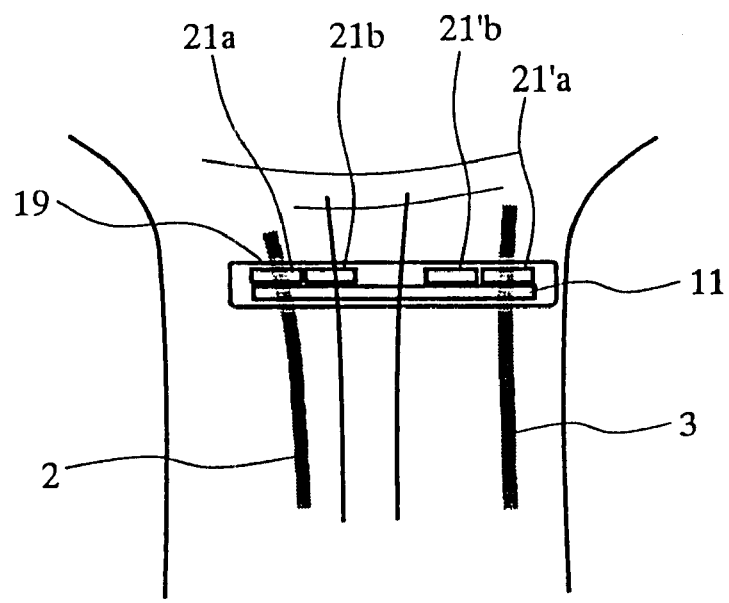
Figure 9A:
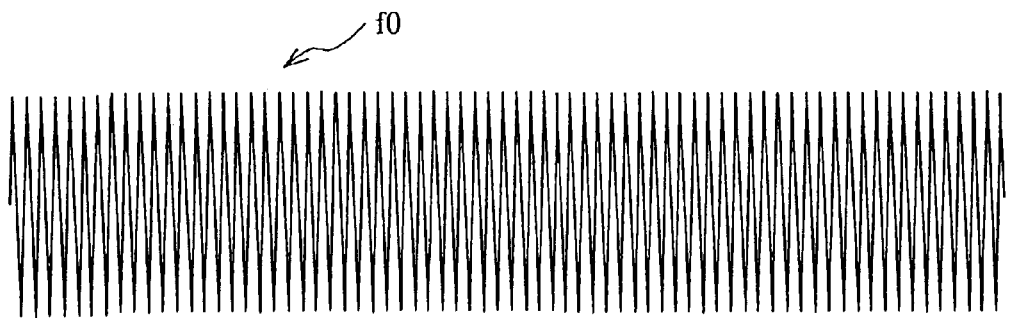
FIGS. 9(a) and 9(b) are diagrams showing changes in the frequency of ultrasound by the Doppler effect.
Figure 9B:
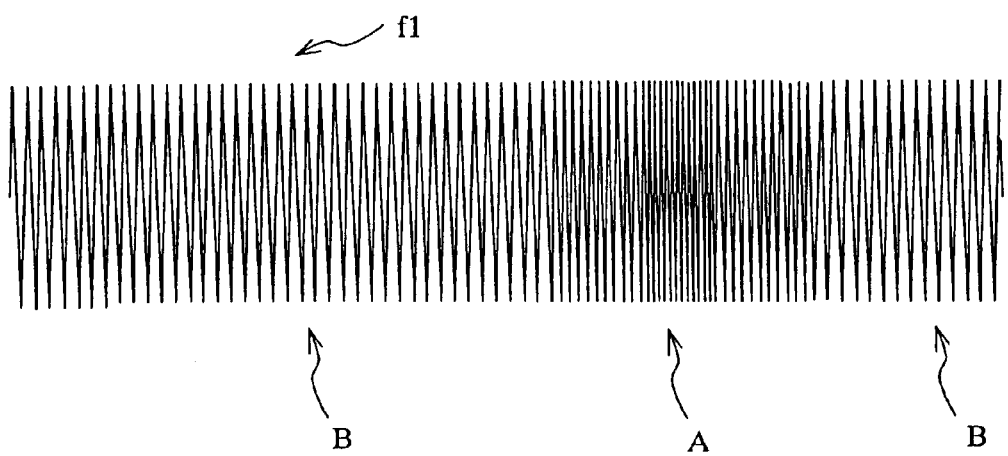

FIGS. 8(a) and 8(b) are diagrams showing examples of modification of the sensors.

In the example shown in FIG. 8(a), a pair of emitting elements 11a and 11b and a pair of receiving elements 21a and 21b are provided in sensor 19, and a pair of emitting elements 11'a and 11'b and a pair of receiving elements 21'a and 21'b are provided in sensor 19'.

In a pulse wave detection device using the sensors shown in FIG. 8(a), switch circuit 10 operates for switching between emission from emitting elements 11a and 11b for measurement on radial artery 2 and emission from emitting elements 11'a and 11'b for measurement on ulnar artery 3. Similarly, switch circuit 20 operates for switching between receiving by receiving elements 21a and 21b and receiving by receiving elements 21'a and 21'b.

Switch circuit 10 may be arranged to separately switch the four emitting elements 11a, 11b, 11'a, and 11'b, and switch circuit 20 may be arranged to separately switch the four receiving elements 21a, 21b, 21'a, and 21'b. In such a case, signal intensity comparison section 75 shown in FIG. 1 determines the effectiveness of each of four processed received sound signals f1', and one of four selection signals is output from control unit 70 to switch circuits 10 and 20 according to the results of determination performed by signal intensity comparison section 75. Signal intensity comparison circuit 77 also operates in a similar manner.

If a plurality of emitting elements 11a, 11b, 11'a, 11'b and a plurality of receiving elements 21a, 21b, 21'a and 21'b are used in the above-described manner, sensors 19 and 19' can be compensated for their misalignments with radial artery 2 and ulnar artery 3 caused by a movement of the wrist, etc., thereby improving the detection performance.

FIG. 8(b) shows one sensor 19 having one emitting element 11 elongated in a direction perpendicular to the longitudinal direction of belt 62 and operated to emit ultrasound to radial artery 2 and to ulnar artery 3. In this case, therefore, there is no need for switch circuit 10, and ultrasound f0 is constantly emitted from the emitting element 11 by drive circuit 12.

The emitting element 11 has such a length as to have an emission range extended to cover both radial artery 2 and ulnar artery 3. In the illustrated example, detection of pulse wave information from radial artery 2 and ulnar artery 3 is performed by one sensor 19, in which one emitting element 11 and a plurality of receiving elements 21a, 21b, 21'a, and 21'b are arranged. This sensor 19 has such as length as to extend across both radial artery 2 and ulnar artery 3, as does emitting element 11.

Since ultrasound from the emitting element 11 is equally emitted to radial artery 2 and to ulnar artery 3, it is not necessary for the pulse wave detection device, to switch the emitting element 11 according to the result of detection of pulse wave information while detecting pulse wave information. Switching of receiving elements 21a and 21b, and switching of receiving elements 21'a and 21'b can also be performed by referring to pulse wave information obtained from the pairs of receiving elements 21a and 21b, and 21'a and 21'b respectively about radial artery 2 and ulnar artery 3. Also, detection may be performed from only one of receiving elements 21a and 21b or 21'a and 21'b having a better output value.

A fifth embodiment of the present invention will next be described.

In the fifth embodiment (not shown), a light sensor is mounted as a portion of each of sensors 19 and 19' (or by the side of the sensor) so that its light receiving surface can be brought into contact with the body surface. If the light sensor receives light, it is determined that processed reflected wave f1' corresponding to the light sensor in the light receiving state is ineffective.

In the fifth embodiment, if a gap is formed between sensor 19 or 19' and the arm, the light sensor mounted in sensor 19 or 19' receives light through the gap. From the light receiving state of the sensor, it is possible to determine that a shift of the pulse wave detection device (body) 60 from the correct position, or the like has occurred, and that the corresponding processed reflected wave f1' does not have adequate effectiveness. Then, control unit 70 shown in FIG. 1 or signal intensity comparison circuit 77 shown in FIG. 7 outputs selection signal A or B, to select one of the sensor 19 on radial artery 2 and the sensor 19' on ulnar artery 3, thereby obtaining pulse wave information.

In the fifth embodiment, a shift of the pulse wave detection device (body) 60 or belt 62 from the correct position, or detection failure can be determined from the existence/nonexistence of light received by light sensors without determining the effectiveness of processed reflected wave f1A' or f1B' by using control unit 70 shown in FIG. 1 or signal intensity comparison circuit 77 as shown in FIG. 7. As a result, pulse wave information can be obtained with improved accuracy.

According to the present invention, a pulse wave detection device is provided which can accurately detect pulse waves without being influenced by noise caused by a movement of the hand, etc.

In the pulse wave detection device according to the present invention, emitting means and receiving means are respectively provided on the radial artery and ulnar artery to detect pulse waves from the radial artery or ulnar artery with reliability no matter what individual differences of wrists.

FIG. 1
10: SWITCH CIRCUIT
12: DRIVE CIRCUIT
13: HIGH-FREQUENCY OSCILLATOR CIRCUIT
20: SWITCH CIRCUIT
31: HIGH-FREQUENCY AMPLIFIER CIRCUIT
32: F/V CONVERTER CIRCUIT
33: DETECTOR CIRCUIT
34: SAMPLE AND HOLD CIRCUIT
35: AMPLIFIER CIRCUIT
36: FILTER CIRCUIT
37: A/D CONVERTER CIRCUIT
42: DISPLAY PANEL
43: BUZZER
44: EXTERNAL APPARATUS
51: LOW-FREQUENCY OSCILLATOR CIRCUIT
70: CONTROL UNIT
71: DISPLAY ELEMENT DRIVE SECTION
72: TIME MEASUREMENT SECTION
73: STORAGE SECTION
74: PULSE RATE COMPUTATION SECTION
75: SIGNAL INTENSITY COMPARISON SECTION
FIG. 6
START
S80: OUTPUT SELECTION SIGNAL A
S81: OBTAIN f1A'
S83: OUTPUT SELECTION SIGNAL B
S84: OBTAIN f1B'
S86: PREDETERMINED TIME ELAPSED?
S87: SOUND BUZZER
END
FIG. 7
10: SWITCH CIRCUIT
12: DRIVE CIRCUIT
13: HIGH-FREQUENCY OSCILLATOR CIRCUIT
20: SWITCH CIRCUIT
31: HIGH-FREQUENCY AMPLIFIER CIRCUIT
32: F/V CONVERTER CIRCUIT
33: DETECTOR CIRCUIT

34: SAMPLE AND HOLD CIRCUIT
38: PULSE RATE COMPUTATION SECTION
41: DISPLAY UNIT
77: SIGNAL INTENSITY COMPARISON SECTION

What is claimed is:

1. A device for detecting pulse waves, comprising: a first sensor positionable on a user's wrist above the user's radial artery and having first emitting means for emitting an ultrasound signal toward the radial artery and first receiving means for receiving an ultrasound signal emitted from the first emitting means and reflected by blood flowing in the radial artery; a second sensor positionable on the user's wrist above the user's ulnar artery and having second emitting means for emitting an ultrasound signal toward the ulnar artery and second receiving means for receiving an ultrasound signal emitted from the second emitting means and reflected by blood flowing in the ulnar artery; pulse wave information acquisition means for acquiring pulse wave information based on pulse waves from the ultrasound signals received by one of the first receiving means and the second receiving means; and output means for outputting the pulse wave information acquired by the pulse wave information acquisition means; wherein the first and second sensors are adjacent each other along a line extending about a circumference of the user's wrist.

2. A device for detecting pulse waves according to claim 1; further comprising effectiveness determination means for determining whether the ultrasound signals received by the first receiving means and the second receiving means are effective for detecting the pulse wave information; and wherein the pulse wave information acquisition means acquires pulse wave information based on pulse waves detected from the ultrasound signal recognized as effective by the effectiveness determination means.

3. A device for detecting pulse waves according to claim 2; further comprising switching means for selecting one of the first sensor or the second sensor when the effectiveness determination means determines that the ultrasound signal received by the other one of the first receiving means and the second receiving means is ineffective.

4. A device for detecting pulse waves according to claim 3; wherein the switching means selects the first sensor after a lapse of a predetermined period of time from a time when the switching means has selected the second sensor.

5. A device for detecting pulse waves according to claim 2; further comprising indication means for indicating that the ultrasound signals received by the first receiving means and the second receiving means are ineffective when the effectiveness determination means has determined that the ultrasound signals received by the first receiving means and the second receiving means are ineffective.

6. A device for detecting pulse waves according to claim 3; further comprising indication means for indicating that the ultrasound signals received by the first receiving means and the second receiving means are ineffective when the effectiveness determination means has determined that the ultrasound signals received by the first receiving means and the second receiving means are ineffective.

7. A device for detecting pulse waves according to claim 4; further comprising indication means for indicating that the ultrasound signals received by the first receiving means and the second receiving means are ineffective when the effectiveness determination means has determined that the ultrasound signals received by the first receiving means and the second receiving means are ineffective.

8. A device for detecting pulse waves, comprising: a first sensor positionable on a user's wrist above the user's radial artery and having a first transmitter for transmitting ultrasound signals toward the user's radial artery and a first receiver for receiving ultrasound signals transmitted from the first transmitter and reflected by blood flowing in the radial artery; a second sensor positionable on the user's wrist above the user's radial artery and having a second transmitter for transmitting ultrasound signals toward the user's ulnar artery and a second receiver for receiving ultrasound signals transmitted from the second transmitter and reflected by blood flowing in the ulnar artery; a pulse wave information acquisition circuit for acquiring pulse wave information in accordance with pulse waves detected from the ultrasound signals received by one of the first receiver and the second receiver; and an output circuit for outputting the pulse wave information acquired by the pulse wave information acquisition circuit; wherein the first and second sensors are adjacent each other along a line extending about a circumference of the user's wrist.

9. A device for detecting pulse waves according to claim 1; wherein the first and second sensors are provided on an inner surface of a wriststrap of a wristwatch so as to be disposed against the user's wrist when the wristwatch is worn on the user's wrist.

10. A device for detecting pulse waves according to claim 1; wherein the pulse wave information acquired by the pulse wave information acquisition means comprises the user's pulse rate.

11. A device for detecting pulse waves according to claim 10; further comprising a display for displaying the pulse rate.

12. A device for detecting pulse waves according to claim 11; wherein the display provides a visual indication of which of the first and second sensors has been selected.

13. A device for detecting pulse waves according to claim 11; wherein the display provides a visual indication of a relative signal strength of the ultrasound signal received by the receiving means of the driven sensor.

14. A device for detecting pulse waves according to claim 1; further comprising a display for displaying the pulse wave information.

15. A device for detecting pulse waves according to claim 14; wherein the display provides a visual indication of which of the first and second sensors has been selected.

16. A device for detecting pulse waves according to claim 14; wherein the display provides a visual indication of a relative signal strength of the ultrasound signal received by the receiving means of the driven sensor.

17. A device for detecting pulse waves according to claim 1; wherein the first and second sensors comprise Doppler sensors.

18. A device for detecting pulse waves according to claim 1; further comprising a housing for containing the pulse wave information acquisition means and the output means, and having a wriststrap on which the first sensor and the second sensor are mounted.

19. A device for detecting pulse waves according to claim 18; further comprising a timepiece movement contained in the housing.

20. A device for detecting pulse waves according to claim 2; wherein the effectiveness determination means determines that a received ultrasonic signal is effective when a magnitude of the received ultrasonic signal is within a predetermined range.

21. A wrist-wearable pulse detector comprising: a housing; a wrist strap attached to the housing for removably attaching the housing to a user's wrist; a first sensor provided on the wrist strap so as to be positioned over the user's radial artery when the pulse detector is attached to the user's wrist, the first sensor having a first emitter for emitting an ultrasound signal toward the radial artery and a first receiver for receiving a first ultrasound signal emitted from the first emitter and reflected by blood flowing in the radial artery; a second sensor provided on the wrist strap so as to be positioned over the user's ulnar artery when the pulse detector is attached to the user's wrist, the second sensor having a second emitter for emitting an ultrasound signal toward the ulnar artery and a second receiver for receiving a second ultrasound signal emitted from the second emitter and reflected by blood flowing in the ulnar artery; and a control circuit for selectively driving one of the first and second sensors based on the relative strength of the received first and second ultrasound signals and calculating pulse information based on the ultrasound signal received by the driven sensor.

22. A wrist-wearable pulse detector according to claim 21; further comprising a display for displaying the calculated pulse information.

23. A wrist-wearable pulse detector according to claim 21; wherein the display provides a visual indication of which one of the first and second sensors is being driven.

24. A wrist-wearable pulse detector according to claim 21; wherein the display provides a visual indication of a relative signal strength of the ultrasound signal received by the receiver of the driven sensor.

25. A wrist-wearable pulse detector according to claim 21; wherein the control circuit determines whether the first and second ultrasound signals are effective for calculating the pulse information by determining whether the first and second ultrasonic signals are within a predetermined range, and preferentially drives the first sensor when the first ultrasound signal is effective for calculating the pulse information.

26. A wrist-wearable pulse detector according to claim 24; wherein the control circuit calculates the pulse information based on one of the first and second ultrasound signals recognized as effective by the effectiveness determining circuit.

* * * * *